(12) United States Patent
Shangguan et al.

(10) Patent No.: US 11,679,279 B2
(45) Date of Patent: *Jun. 20, 2023

(54) SYSTEM AND METHOD FOR ADAPTIVE RADIATION THERAPY

(71) Applicant: SHANGHAI UNITED IMAGING HEALTHCARE CO., LTD., Shanghai (CN)

(72) Inventors: Xiaoqing Shangguan, Shanghai (CN); Chengcheng Rong, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 193 days.

This patent is subject to a terminal disclaimer.

(21) Appl. No.: 17/189,129

(22) Filed: Mar. 1, 2021

(65) Prior Publication Data

US 2021/0187327 A1    Jun. 24, 2021

Related U.S. Application Data

(63) Continuation of application No. 16/236,419, filed on Dec. 29, 2018, now Pat. No. 10,933,257, which is a continuation of application No. PCT/CN2017/120389, filed on Dec. 30, 2017.

(51) Int. Cl.
*A61N 5/10* (2006.01)

(52) U.S. Cl.
CPC ......... *A61N 5/1071* (2013.01); *A61N 5/1038* (2013.01); *A61N 5/1039* (2013.01); *A61N 2005/1072* (2013.01)

(58) Field of Classification Search
CPC .. A61N 5/1071; A61N 5/1038; A61N 5/1039; A61N 2005/1072
See application file for complete search history.

(56) References Cited

U.S. PATENT DOCUMENTS

| | | | |
|---|---|---|---|
| 10,933,257 B2* | 3/2021 | Shangguan | A61N 5/1071 |
| 2002/0122530 A1 | 9/2002 | Erbel et al. | |
| 2007/0041497 A1 | 2/2007 | Schnarr et al. | |
| 2007/0041499 A1 | 2/2007 | Lu et al. | |

(Continued)

FOREIGN PATENT DOCUMENTS

| | | |
|---|---|---|
| CN | 104548372 A | 4/2015 |
| CN | 106920234 A | 7/2017 |
| CN | 107224678 A | 10/2017 |

OTHER PUBLICATIONS

International Search Report in PCT/CN2017/120389 dated Sep. 27, 2018, 5 pages.

(Continued)

*Primary Examiner* — Courtney D Thomas
(74) *Attorney, Agent, or Firm* — Metis IP LLC

(57) ABSTRACT

The disclosure relates to a system and method for adapt a treatment plan. The method may include: obtaining an initial treatment plan of a region of interest, wherein the initial treatment plan includes a first initial treatment fraction and a second initial treatment fraction; causing a radiation treatment device to deliver the first initial treatment fraction; obtaining a treatment record related to the first initial treatment fraction; and generating an updated second treatment fraction based on the second initial treatment fraction and the treatment record.

20 Claims, 9 Drawing Sheets

(56) References Cited

U.S. PATENT DOCUMENTS

| | | |
|---|---|---|
| 2010/0020931 A1 | 1/2010 | Otto et al. |
| 2011/0112351 A1 | 5/2011 | Fordyce, II et al. |
| 2012/0065994 A1 | 3/2012 | Carter et al. |
| 2015/0367145 A1 | 12/2015 | Sjölund et al. |
| 2016/0378948 A1 | 12/2016 | Kuusela et al. |

OTHER PUBLICATIONS

Written Opinion in PCT/CN2017/120389 dated Sep. 27, 2018, 4 pages.
First Office Action in Chinese Application No. 201780005158.X dated Nov. 2, 2020, 26 pages.

* cited by examiner

SYSTEM AND METHOD FOR ADAPTIVE RADIATION THERAPY

CROSS REFERENCE TO RELATED APPLICATION

This present application is a continuation of U.S. patent application Ser. No. 16/236,419, filed on Dec. 29, 2018, which is a continuation application of International Application No. PCT/CN2017/120389 filed on Dec. 30, 2017, the entire contents of which are incorporated herein by reference.

TECHNICAL FIELD

The present disclosure generally relates to systems and methods for radiation therapy, and more particularly, to systems and methods for generating an adaptive radiation therapy treatment plan based on a forecasting of changes of a radiotherapy target.

BACKGROUND

Radiation therapy is widely used in cancer therapy and is also indicated for several other health conditions. Conventionally, a radiation therapy treatment plan (also referred herein as an initial treatment plan) for a cancer patient is generated before treatment starts. The treatment plan may be delivered to the patient during several treatment fractions, spread over a treatment period of multiple days. However, during the treatment period, the anatomy of the tumor or other tissues (e.g., tissue surrounding the tumor) may change. For example, the tumor may grow, deform, or shrink. Accordingly, the treatment plan may need to be updated. Thus, it may be desirable to develop systems and methods for generating an adaptive radiation therapy treatment plan during the course of the treatment period.

SUMMARY in a first aspect of the present disclosure, a system for adapt a treatment plan may be provided. The system may include at least one storage medium and at least one processor. The at least one storage medium may include a set of instructions. The at least one processor may be configured to cause the system to obtain an initial treatment plan of a region of interest, wherein the initial treatment plan includes a first initial treatment fraction and a second initial treatment fraction. The at least one processor may be configured to cause the system to cause a radiation treatment device to deliver the first initial treatment fraction. The at least one processor may be configured to cause the system to obtain a treatment record related to the first initial treatment fraction. The at least one processor may be configured to cause the system to generate an updated second treatment fraction based on the second initial treatment fraction and the treatment record.

In some embodiments, the treatment record may include one or more machine radiation parameters related to the radiation treatment device and one or more geometrical parameters related to the radiation treatment device.

In some embodiments, the one or more machine radiation parameters related to the radiation treatment device may include a dose rate, a delivery duration of a beam, or a modality type of the beam.

In some embodiments, the one or more geometrical parameters relating to the radiation treatment device may include at least one of position information of a table of the radiation treatment device, position information of a gantry of the radiation treatment device, or position information of a collimator of the radiation treatment device.

In some embodiments, the at least one processor may be further configured to cause the system to determine one or more transformations of the region of interest based on a forecasting model and the initial treatment plan.

In some embodiments, the at least one processor may be further configured to obtain one or more characteristic parameters related to a first object. The at least one processor may be further configured to retrieve a reference record set based on the one or more first characteristic parameters related to the first object. The at least one processor may be further configured to generate a forecasting model related to the first object based on the reference record set. The at least one processor may be further configured to update the forecasting model based on the initial treatment plan.

In some embodiments, the one or more characteristic parameters may include at least one of an age of the first object, a gender of the first object, tumor location information of the first object, a tumor type of the first object, a tumor size of the first object, tumor stage information of the first object, or a dose distribution related to a tumor.

In some embodiments, the first initial treatment fraction may include an initial treatment parameter set. To generate the updated second treatment fraction based on the second initial treatment fraction and the treatment record, the at least one processor may be further configured to cause the system to generate an actual treatment parameter set of the first initial treatment fraction based on the treatment record. The at least one processor may be further configured to generate the updated second treatment fraction based on the actual treatment parameter set.

In some embodiments, the at least one processor may be further configured to cause the system to obtain a first image of the region of interest by a first scan of the region of interest and a second image of the region of interest by a second scan of the region of interest. The at least one processor may be further configured to cause the system to determine a contour of the region of interest in the second image based on a registration matrix and the first image. The at least one processor may be further configured to cause the system to determine the updated second treatment fraction based on the contour of the region of interest.

In a second aspect of the present disclosure, a method for adapting a treatment plan is provided. The method may be implemented on at least one device each of which has at least one processor and storage. The method may include: obtaining an initial treatment plan of a region of interest, wherein the initial treatment plan includes a first initial treatment fraction and a second initial treatment fraction; causing a radiation treatment device to deliver the first initial treatment fraction; obtaining a treatment record related to the first initial treatment fraction; and generating an updated second treatment fraction based on the second initial treatment fraction and the treatment record.

In some embodiments, the treatment record may include one or more machine radiation parameters related to the radiation treatment device and one or more geometrical parameters related to the radiation treatment device.

In some embodiments, the one or more machine radiation parameters related to the radiation treatment device may include a dose rate, a delivery duration of a beam, or a modality type of the beam.

In some embodiments, the one or more geometrical parameters relating to the radiation treatment device may include at least one of position information of a table of the radiation treatment device, position information of a gantry of the radiation treatment device, or position information of a collimator of the radiation treatment device.

In some embodiments, the method may further include determining one or more transformations of the region of interest based on a forecasting model and the initial treatment plan.

In some embodiments, to generate the forecasting model, the method may further include: obtaining one or more characteristic parameters related to a first object; retrieving a reference record set based on the one or more first characteristic parameters related to the first object; generating a forecasting model related to the first object based on the reference record set; and updating the forecasting model based on the initial treatment plan.

In some embodiments, the one or more characteristic parameters may include at least one of an age of the first object, a gender of the first object, tumor location information of the first object, a tumor type of the first object, a tumor size of the first object, tumor stage information of the first object, or a dose distribution related to a tumor.

In some embodiments, the first initial treatment fraction may include an initial treatment parameter set, and to generate the updated second treatment fraction based on the second initial treatment fraction and the treatment record, the method may further include: generating an actual treatment parameter set of the first initial treatment fraction based on the treatment record; and generating the updated second treatment fraction based on the actual treatment parameter set.

In a third aspect of the present disclosure, a non-transitory computer readable medium is provided. The non-transitory computer readable medium may include executable instructions. When the instructions are executed by at least one processor, the instructions may cause the at least one processor to implement a method. The method may include obtaining an initial treatment plan of a region of interest, wherein the initial treatment plan includes a first initial treatment fraction and a second initial treatment fraction; causing a radiation treatment device to deliver the first initial treatment fraction; obtaining a treatment record related to the first initial treatment fraction; and generating an updated second treatment fraction based on the second initial treatment fraction and the treatment record.

In a fourth aspect of the present disclosure, a system for adapt a treatment plan may be provided. The system may include at least one storage medium and at least one processor. The at least one storage medium may include a set of instructions. The at least one processor may be configured to cause the system to obtain a treatment plan of a region of interest. The at least one processor may be configured to cause a radiation treatment device to deliver treatment radiation to an object based on the treatment plan. The at least one processor may be configured to cause the system to obtain a treatment record related to the treatment plan. The at least one processor may be configured to generate an actual treatment parameter set based on the treatment record.

In a fifth aspect of the present disclosure, a method for adapting a treatment plan may be provided. The method may be implemented on at least one device each of which has at least one processor and storage. The method may include: obtaining a treatment plan of a region of interest; causing a radiation treatment device to deliver treatment radiation to an object based on the treatment plan; obtaining a treatment record related to the treatment plan, generating an actual treatment parameter set based on the treatment record.

In a sixth aspect of the present disclosure, a system for generating an actual dose distribution of an object may be provided. The system may include at least one storage medium and at least one processor. The at least one storage medium may include a set of instructions. The at least one processor may be configured to cause the system to obtain a treatment plan of a region of interest. The at least one processor may be configured to cause a radiation treatment device to deliver treatment radiation to an object based on the treatment plan. The at least one processor may be configured to obtain a first image of the region of interest relating to a first scan of the region of interest. The at least one processor may be configured to obtain a treatment record related to the treatment plan. The at least one processor may be configured to generate an actual treatment parameter set according to the treatment record. The at least one processor may be configured to generate an actual dose distribution of the object according to the actual treatment parameter set and the first image.

In a seventh aspect of the present disclosure, a method for generating an actual dose distribution of an object may be provided. The method may include obtaining a treatment plan of a region of interest; causing a radiation treatment device to deliver treatment radiation to an object based on the treatment plan; obtaining a first image of the region of interest relating to a first scan of the region of interest; obtaining a treatment record related to the treatment plan; generating an actual treatment parameter set according to the treatment record; generating an actual dose distribution of the object according to the actual treatment parameter set and the first image.

In an eighth aspect of the present disclosure, a system for forecasting transformation of a region of interest may be provided. The system may include at least one storage medium and at least one processor. The at least one storage medium may include a set of instructions. The at least one processor may be configured to obtain one or more characteristic parameters related to a first object. The at least one processor may be configured to retrieve a reference record set based on the one or more characteristic parameters related to the first object. The at least one processor may be configured to generate a forecasting model based on the reference record set. The at least one processor may be configured to determine one or more transformations of a region of interest of the first object based on the forecasting model and a treatment plan related to the first object.

In a ninth a method for forecasting transformation of a region of interest may be provided. The method may include obtaining one or more characteristic parameters related to a first object; retrieving a reference record set based on the one or more characteristic parameters related to the first object; generating a forecasting model based on the reference record set; and determining one or more transformations of a region of interest of the first object based on the forecasting model and a treatment plan related to the first object.

Additional features will be set forth in part in the description which follows; and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

Figure 2:
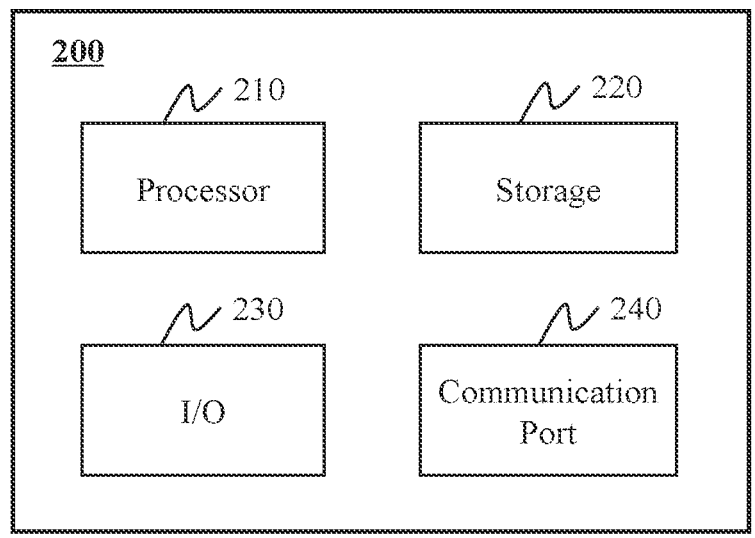
FIG. 2 is a schematic diagram illustrating an exemplary computing device on which the radiation therapy system can be implemented, according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an erasable programmable read-only memory (EPROM). It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when as used herein, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and components for non-invasive imaging and/or treatment, such as for disease diagnosis, treatment or research purposes. In some embodiments, the system may be a radiation therapy (or referred to as radiotherapy) system, a computed tomography (CT) system, an emission computed tomography (ECT) system, an X-ray photography system, a positron emission tomography (PET) system, or the like, or any combination thereof. For illustration purposes, the disclosure describes systems and methods for radiation therapy. The term "image" as used herein may refer to a 2D image, a 3D image, or a 4D image. In some embodiments, the term "image" may refer to an image of a region of interest (ROI) of a patient. The term "region of interest" or "ROI" as used herein may refer to a part of an image along a line, in two spatial dimensions, in three spatial dimensions, or any of the proceedings as they evolve as a function of time. The ROI may be a region of a patient including at least part of a malignant tissue (e.g., a tumor, a cancer-ridden organ, or non-cancerous target of radiation therapy). Additionally or alternatively, the ROI may include another tissue, such as a tissue surrounding the malignant tissue. The image may be a CT image, an Electronic Portal Image Device (EPID) image, a fluoroscopy image, an ultrasound image, a PET image, or an MRI, image. The term "planning image" as used herein may refer to an image according to which a treatment plan is made.

The term "treatment plan" in this disclosure may describe how a radiation therapy is performed on a patient, or more specifically, how one or more beams are delivered to an ROI of a patient during a course of treatment lasting days or weeks or months. The treatment plan may provide a total dosage (e.g., 0.1 Gy, 10 Gy, 50 Gy, 100 Gy, etc.) and a total dose distribution in the ROI. In some embodiments, the treatment plan may be a treatment plan determined at the beginning of the course of a radiotherapy. Before a patient begins to receive radiation therapy (e.g., days before or weeks before), one or more planning images may be taken, and the treatment plan may be designed for the patient based on the planning image. The planning image may include information related to a treatment target, one or more organs at risk, and the external contour of the patient, or the like, or a combination thereof.

Since it may be unbearable for a patient to subject to the total dose quantity prescribed by the treatment plan in one treatment fraction, a treatment plan may be divided into a plurality of treatment fractions. The patient may receive a treatment fraction a day, or two treatment fractions a day. The treatment fraction may provide, e.g., a fractional dosage (e.g., 0.1 Gy, 1 Gy, 2 Gy, etc.), a fractional dose distribution in the ROI, or the like, or a combination thereof. The sum of fraction dosages of all the plurality of treatment fractions may equal the total dosage of the treatment plan.

Additionally or alternatively, a treatment fraction may include one or more fields. A map of a fluence delivered by each beam emitted from a radiation source to a cross section of the ROI may be referred to as a field. A field may include one or more segments. In some embodiments, the shape of the ROI may be regular (e.g., circular, square, triangle, etc.), or irregular. The field may include one or more segments with different shapes to conform to the shape of the ROI. In this way, a beam of the field may irradiate the ROI and not another anatomical structure adjacent to the ROI (e.g., an organ at risk). A field of a treatment fraction may be characterized by a treatment parameter set. For example, a treatment parameter set of a field of a treatment fraction may include a field dose, a radiation beam direction, a radiation beam shape, the cross-sectional area of a radiation beam, or the like, or any combination thereof. The sum of the field doses of all the one or more fields of a treatment fraction may equal the fraction dose of the treatment fraction.

A treatment fraction may provide an operation parameter set related to a field describing how a radiation treatment device delivers a field of the treatment fraction. The operation parameter set may include a machine radiation parameter and a geometrical parameter. The radiation parameter may include a dose rate (e.g., MUs/min) provided by a radiation source, the duration of radiation; a modality type information (e.g., photons, electrons, etc.) provided by the radiation source, or the like, or any combination thereof. The geometrical parameter may include an angle of a gantry at a certain time, a rotation speed of the gantry at a certain time, an angle of a collimator at a certain time, a rotation speed of the collimator at a certain time, a leaf setting parameter of a multi-leaf collimator (e.g., X1, X2, Y1, and Y2 values for individual leaves of the multi-leaf collimator, etc.), position and angle of a table at a certain time, or the like, or a combination thereof.

The term "image data" as used herein may refer to radiation data (e.g., CT data and projection data corresponding to the radiation data. This is not intended to limit the scope the present disclosure. For persons having ordinary skills in the art, a certain number of variations, changes, and/or modifications may be deduced under the guidance of the present disclosure. Those variations, changes, and/or modifications do not depart from the scope of the present disclosure.

In this disclosure, before the treatment plan is prescribed, a planning image of the treatment plan regarding an object may be obtained. Before a treatment fraction (e.g., on the day of treatment, or hours before the treatment, or minutes before the treatment, or seconds before the treatment), a CT scan may be performed to generate a first image. The first image may be used to guide radiation delivery during the treatment fraction. A first treatment fraction may be performed. A treatment record related to the first treatment fraction may be generated. The treatment plan may be updated based on the treatment record.

Figure 1:
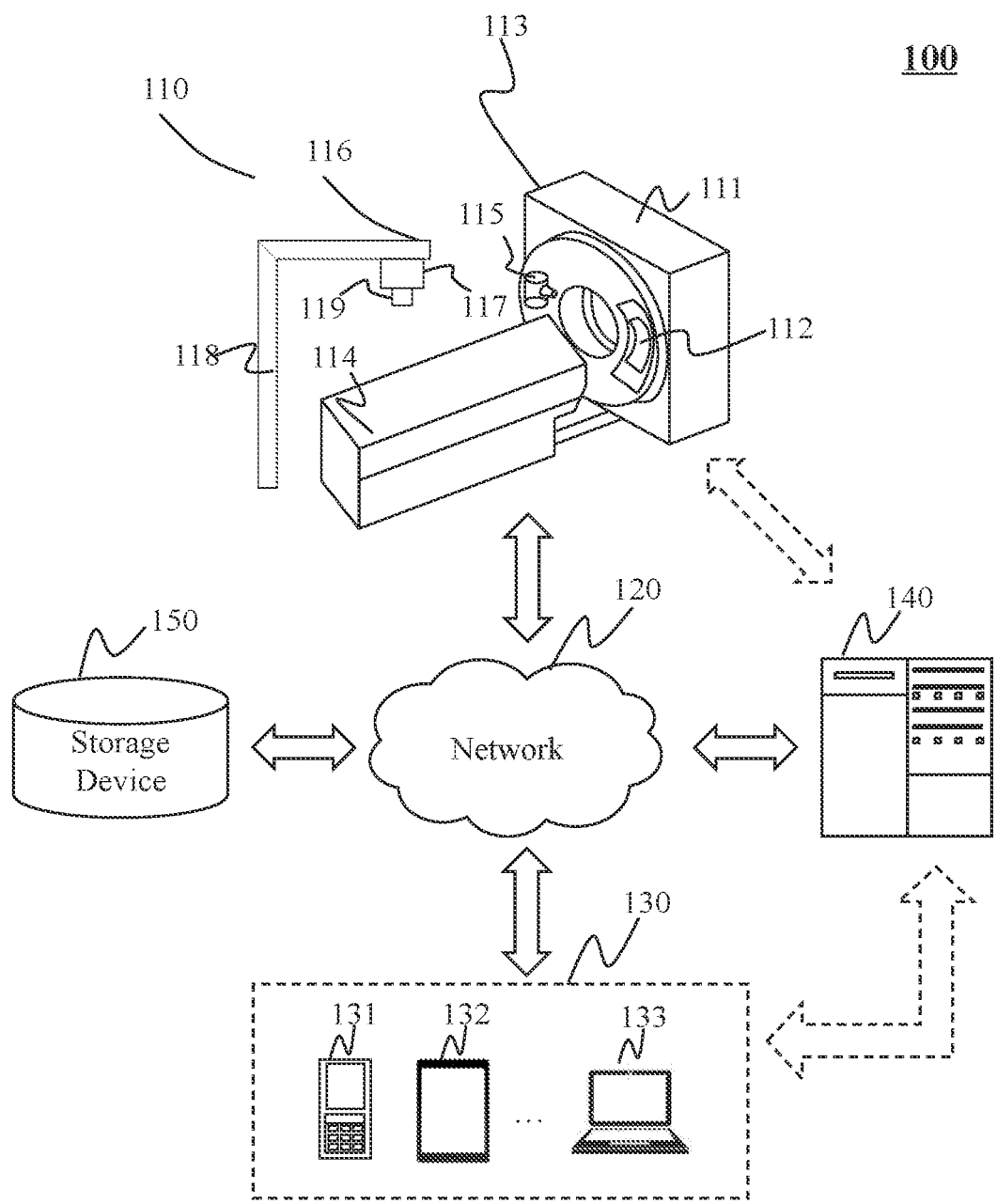
FIG. 1 is a schematic diagram illustrating an exemplary radiation therapy system according to some embodiments of the present disclosure.

FIG. 1 is a schematic diagram illustrating an exemplary radiation therapy system 100 according to some embodiments of the present disclosure. The radiation therapy system 100 may include an imaging-treatment device 110, a network 120, one or more terminals 130, a processing device 140, and a storage device 150.

The imaging-treatment device 110 may include an imaging component 113, a treatment component 116, a table 114, or the like. The imaging component 113 may include an imaging radiation source 115, a detector 112, a gantry 111, or the like. The imaging radiation source 115 and the detector 112 may be mounted on the gantry 111. The treatment component 116 may include a treatment radiation source 117, a gantry 118, and a collimator 119. The treatment radiation source 117 may be a linear accelerator (LINAC). The collimator 119 may control the shape of the radioactive rays generated by the treatment radiation source 117. In some embodiments, the imaging component 113 and the treatment component 116 may share a same gantry. For example, the treatment radiation source 117 may be mounted on the gantry 111. An object may be placed on the table 114 for treatment and/or scan.

The imaging component 113 may generate an image of the object before, during, and/or after a treatment fraction. The imaging component may include a computed tomography (CT) component, an ultrasound imaging component, a fluoroscopy imaging component, a magnetic resonance imaging (MRI) component, a single photon emission computed tomography (SPECT) component, a positron emission tomography (PET) component, or the like, or any combination thereof.

The imaging radiation source 115 may emit radioactive rays to the object. The detector 112 may detect at least a portion of the radiation events (e.g., x-ray photons, gamma-ray photons) traversing a scanned object (e.g., a patient). In some embodiments, the detector 112 may include one or more detector units. The detector units may include a scintillation detector (e.g., a cesium iodide detector, a gadolinium oxysulfide detector), a gas detector, etc. The detector unit may include a single-row detector and/or a multi-rows detector.

In some embodiments, the imaging component 113 may be a cone beam computed tomography (CBCT) imaging component. The CBCT imaging component may perform a CBCT scan on the object by emitting cone beam X-rays to the object. In some embodiments, the imaging component may be a multi-slice CT (MSCT) imaging component. The MSCT imaging component may perform an MSCT scan of the object. In some embodiments, the imaging component may be an integrated CT imaging component that can perform a CBCT scan and an MSCT scan. The treatment component 116 may deliver radiation treatment to the object (e.g., a patient). The treatment radiation source 117 may emit treatment radiations towards the object.

In some embodiments, the imaging component 113 may be spaced by a distance from the treatment component 116. In some embodiments, the gantry 111 of the imaging component and the gantry 118 of the treatment component may share an axis of rotation. The object may be positioned in different positions on the table 114 for imaging and treatment. In some embodiments, the imaging radiation source 115 and the treatment radiation source 117 may be integrated as one radiation source to image and/or treat the object.

In some embodiments, the radiation therapy system 100 may include a radiation treatment device and a CT scanner. The radiation treatment device may include one or more components that are the same as or substantially similar to those of the imaging-treatment device 110. For example, the radiation treatment device may include a treatment component, a gantry, a table, and a detection region. In some embodiments, the CT scanner may be a CBCT scanner, or an MSCT scanner, or the like, or any combination thereof. The images generated based on the CT scan may be stored in a storage device, e.g., the storage device 150, in the radiation therapy system 100 for adapting radiation therapy planning.

The network 120 may include any suitable network that can facilitate the exchange of information and/or data for the radiation therapy system 100. In some embodiments, one or more components of the radiation therapy system 100 (e.g., the imaging-treatment device 110, the terminal 130, the processing device 140, the storage device 150, etc.) may communicate information and/or data with one or more other components of the radiation therapy system 100 via the network 120. For example, the processing device 140 may obtain image data from the imaging-treatment device 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LIE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WEAN), a metropolitan area network (MAN), a public telephone switched network (PSTN), a Bluetooth™ network, a ZigBee™ network, a near field communication (NEC) network, or the like, or any combination thereof. In some embodiments, the network 120 may include one or more network access points. For example, the network 120 may include wired and/or wireless network access points such as base stations and/or internet exchange points through which one or more components of the radiation therapy system 100 may be connected to the network 120 to exchange data and/or information.

Figure 3:
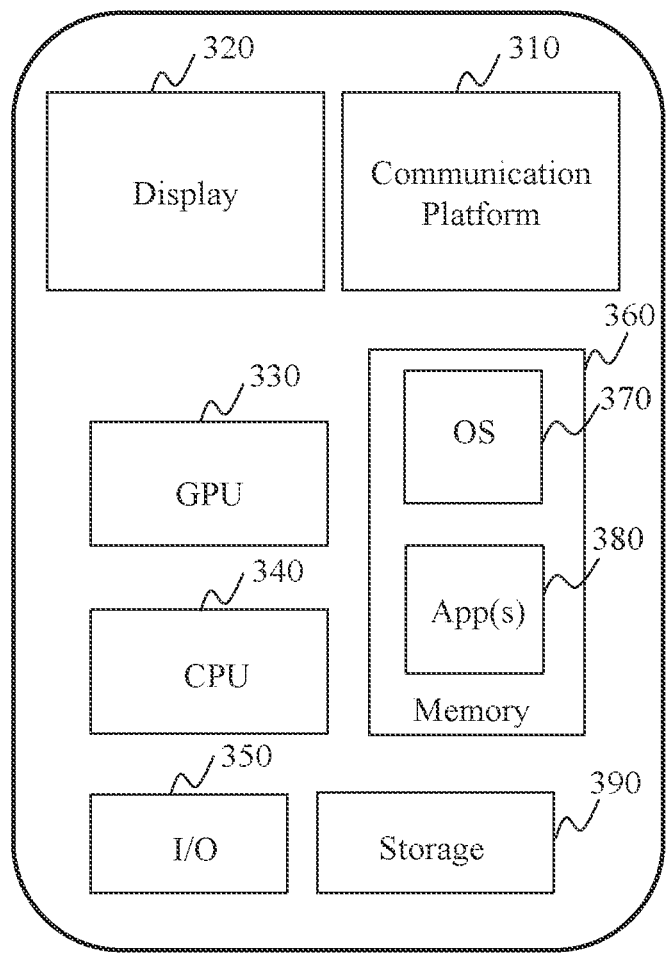
FIG. 3 is a schematic diagram illustrating hardware and/or software components of an exemplary mobile device according to some embodiments of the present disclosure.

The terminal(s) 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™ etc. In some embodiments, the terminal(s) 130 may be part of the processing device 140.

The processing device 140 may process data and/or information obtained from the imaging-treatment device 110, the terminal 130, and/or the storage device 150. In some embodiments, the processing device 140 may be a single server or a server group. The server group may be centralized or distributed. In some embodiments, the processing device 140 may be local or remote. For example, the processing device 140 may access information and/or data stored in the imaging-treatment device 110, the terminal 130, and/or the storage device 150 via the network 120. As another example, the processing device 140 may be directly connected to the imaging-treatment device 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the radiation therapy system 100 (e.g., the processing device 140, the terminal 130). One or more components of the radiation therapy system 100 may access the data or instructions stored in the storage device 150 via the network 120. In some embodiments, the storage device 150 may be directly connected to or communicate with one or more other components of the radiation therapy system 100 (e.g., the processing device 140, the terminal 130). In some embodiments, the storage device 150 may be part of the processing device 140.

FIG. 2 is a schematic diagram illustrating an exemplary computing device 200 on which at least a portion of the radiation therapy system 100 can be implemented, according to some embodiments of the present disclosure. As illustrated in FIG. 2, the computing device 200 may include a processor 210, storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the imaging-treatment device 110, the storage 150, terminal(s) 130, and/or any other component of the radiation therapy system. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging-treatment device 110, the storage 150, the terminal(s) 130, and/or any other component of the radiation therapy system 100. In some embodiments, the storage 220 may include a mass storage, removable storage, a volatile read-and-write memory, a read-only memory (ROM), or the like, or a combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 120 and the imaging-treatment device 110, the storage 150, and/or the terminal(s) 130. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation therapy system 100 via the network 120.

Figure 4:
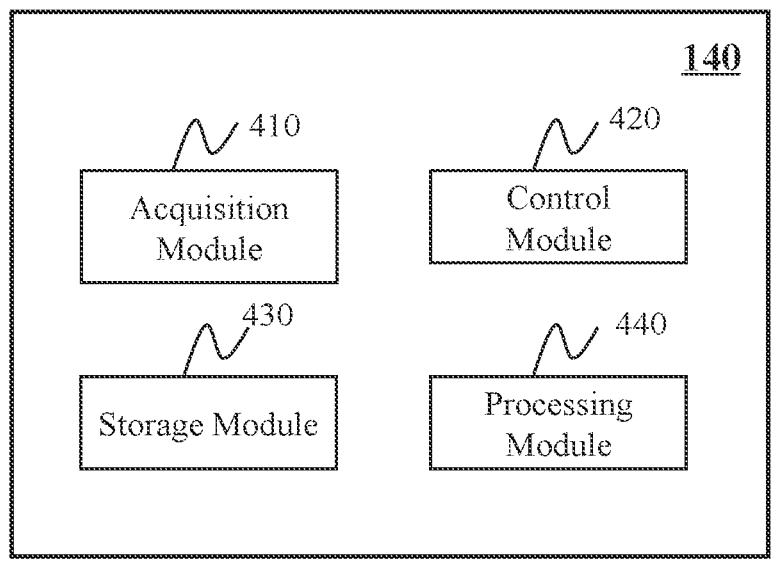
FIG. 4 is a block diagram illustrating an exemplary processing device according to some embodiments of the present disclosure.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed, FIG. 4 is a block diagram illustrating an exemplary processing device 140 according to some embodiments of the present disclosure. The processing device 140 may include an acquisition module 410, a control module 420, a storage module 430, and a processing module 440. The processing device 140 may be implemented on various components (e.g., the computing device 200 as illustrated in FIG. 2, the mobile device 300 as illustrated in FIG. 3).

The acquisition module 410 may acquire data relating to the radiation therapy system 100. The data may include image data associated with the imaging component (e.g., a CBCT imaging component, or an MSCT imaging component) and treatment data associated with the treatment component as described elsewhere in the present disclosure. See, e.g., FIG. 1 and the description thereof. The acquisition module 410 may acquire image data from the detector 112. The image data may be generated based on X-rays that pass through an object. In some embodiments, the imaging radiation source 115 may emit X-rays to the object. At least a portion of the X-rays may pass through the object and be attenuated. At least a portion of the X-rays emitted by the imaging radiation source 115, including at least a portion of the attenuated X-rays, may be detected by the detector 112 and transmitted to the acquisition module 410. In some embodiments, the acquired image data may be transmitted to the storage module 430 to be stored.

The acquisition module 410 may acquire the treatment plan from a storage device in the radiation therapy system 100 (e.g., the storage device 150). Additionally or alternatively, the acquisition module 410 may acquire at least part of the treatment plan from another system, such as a database maintained by, for example, a hospital, or the like. The treatment plan may include one or more treatment fractions. For each of the treatment fraction, the radiation treatment plan may include a plurality of treatment parameters, such as a planned fraction duration, a planned radiation dose, a planned radiation delivery direction, a planned radiation beam shape, a planned radiation beam cross-sectional area, a planned region of interest (ROI), etc.

The acquisition module 410 may obtain one or more characteristic parameters related to an object (e.g., a patient). A characteristic parameter may include at least one of an object characteristic parameter and a target characteristic parameter. The object characteristic parameter may represent a general characteristic of the object including, for example, the age of the object, or the gender of the object, etc. The target characteristic parameter may represent a characteristic of a target, e.g., a tumor.

The control module 420 may execute control information. In some embodiments, the control module 420 may cause the imaging-treatment device 110 to perform a scan of an object, cause the imaging-treatment device 110 to deliver a treatment to the object, cause the processing device 140 to perform data processing, etc. For example, the control module 420 may cause the detector 112 to collect image data in accordance with a preset parameter via a work program customized for a tumor or an anatomical site. For example, the control module 420 may control the imaging-treatment device 110 to send the image data to the processing device 140 for image processing. For example, according to a user's (e.g., a doctor) instruction, the control module 420 may cause the image data associated with the object and corresponding operations to be recorded and/or processed.

The storage module 430 may store information. The information may include image data and/or a treatment record from the acquisition module 410, operation instructions of a user obtained via, e.g., the communication port 240, results generated by the processing module 440, etc. The storage module 430 may store information in the format of text, a digital document, sound, an image, a video, etc. In some embodiments, the storage module 430 may be a storage device of one of various types such as a solid-state hard disk, a mechanical hard disk, a universal serial bus (USB), flash memory, a secure digital (SD) memory card, an optical disk, a random-access memory (RAM), a read-only memory (ROM), etc. In some embodiments, the storage module 430 may be one or more mass storages, for example, a mass storage array managed by one or more controllers. In some embodiments, the storage module 430 may be a local storage device of the processing device 140, an external storage device, a distributed storage device (e.g., cloud storage, etc.) that is communicatively connected via the network 120, etc.

The processing module 440 may process various information including, e.g., image data, a treatment plan, and/or a treatment record. The processing module 440 may process information provided by various modules of the processing device 140. The processing module 440 may process image data and/or a treatment plan acquired by the acquisition module 410, or retrieved from the storage module 430, etc. In some embodiments, the processing module 440 may reconstruct an image based on the image data according to a reconstruction algorithm, generate reports including one or more reconstructed images and/or other related information, and/or perform any other function for image reconstruction in accordance with various embodiments of the present disclosure. Exemplary reconstruction algorithms may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. In some embodiments, the processing module 440 may be one or more processing components or devices, such as a central processing unit (CPU), a graphics processing unit (GPU), a digital signal processor (DSP), a system on a chip (SoC), a microcontroller unit (MCU), etc. In some embodiments, the processing module 440 may also be a specially designed processing component or device with special functions.

In some embodiments, one or more modules illustrated in FIG. 4 may be implemented in at least part of the exemplary radiation therapy system 100 as illustrated in FIG. 1. For example, the acquisition module 410, the control module 420, the storage module 430, and/or the processing module 440 may be integrated into a console (not shown) with a user interface component. Via the console, a user may set parameters for scanning an object, controlling imaging processes, controlling parameters for reconstruction of an image, viewing reconstructed images, provide an instruction regarding the delivery of a treatment plan or a portion thereof, etc. In some embodiments, the console may be implemented via the processing device 140 and/or the terminal 130.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules. However, those variations and modifications also fall within the scope of the present disclosure.

Figure 5:
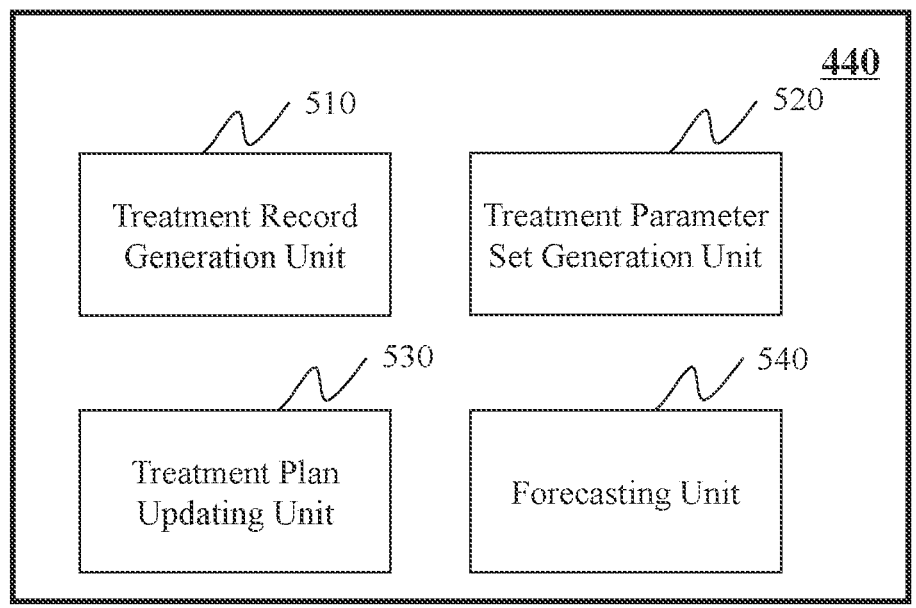
FIG. 5 is a block diagram illustrating an exemplary processing module according to some embodiments of the present disclosure.

FIG. 5 is a block diagram illustrating an exemplary processing module 440 according to some embodiments of the present disclosure. The processing module 440 may include a treatment record generation unit 510, a treatment parameter set generation unit 520, a treatment plan updating unit 530, and a forecasting unit 540.

The treatment record generation unit 510 may generate a treatment record related to the delivery of a treatment fraction relating to an ROI of an object. A treatment record may include an actual operation parameter set, describing how a treatment fraction of a treatment plan is actually performed by the treatment component 116. In some embodiments, a deviation may exist between the actual operation parameter set of the treatment record (e.g., a first initial treatment fraction) and the planned operation parameter set of the initial treatment fraction (e.g., the first initial treatment fraction).

The treatment parameter set generation unit 520 may generate an actual treatment parameter set of a treatment fraction based on the treatment record. An actual treatment parameter set may be a treatment parameter set characterizing the one or more beam fields practically generated by the treatment component 116. The treatment record generation unit 510 may determine the actual treatment parameter set of the treatment fraction based on the treatment record. For example, a field dose of the actual treatment parameter set may be determined based on the dose rate and the radiation duration at a specific angle. As another example, the radiation beam direction or the radiation beam shape of the actual treatment parameter set may be determined based on the geometrical parameter(s) of the treatment record.

The treatment plan updating unit 530 may update a treatment plan based on the treatment record. The treatment plan updating unit 530 may determine whether a deviation exists between an actual operation parameter set obtained from the treatment record of the first initial treatment fraction and the planned operation parameter set of the first initial treatment fraction. The treatment plan updating unit 530 may update the planned operation parameter set of a second initial treatment fraction to generate an updated second treatment fraction based on the deviation.

The forecasting unit 540 may determine whether the ROI of the object transforms. The transformation of a ROI may include, e.g., a shape change (e.g. volume change) of the ROI and/or a position change of the ROI after the object receives the treatment according to the treatment plan (e.g., one or more treatment fractions of the treatment plan). The forecasting unit 540 may determine whether the treatment plan is suitable for the object based on a forecasting model. The forecasting unit 540 may retrieve a reference record set based on one or more characteristic parameters of the object. The forecasting unit 540 may generate the forecasting model related to the object based on the reference record set. The forecasting unit 540 may forecast or estimate, based on the forecasting model, information regarding a target, e.g., a tumor. For instance, the forecasting model may simulate a tumor size (e.g., gross tumor volume) of the object before or after implementing a certain treatment fraction of a treatment plan. The forecasting unit 540 may obtain treatment images generated by scans after a first object receives a treatment according to a treatment fraction, and update the forecasting model based on the target characteristic parameter in the treatment images of the object.

It should be noted that the above descriptions of the processing module 440 are provided for the purposes of illustration, and not intended to limit the scope of the present disclosure. For persons having ordinary skills m the art, various modifications and changes in the forms and details of the application of the above method and system may occur without departing from the principles of the present disclosure. In some embodiments, the processing module 440 may include one or more other units. However, those variations and modifications also fall within the scope of the present disclosure.

Figure 6:
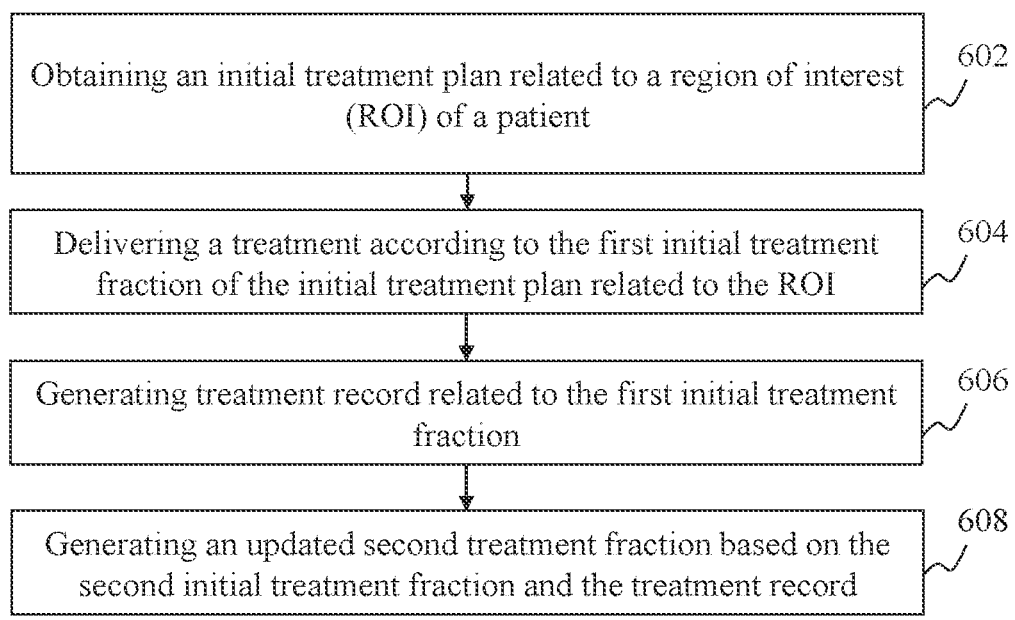
FIG. 6 is a flowchart illustrating an exemplary process for updating a treatment plan for a patient according to some embodiments of the present disclosure.

FIG. 6 illustrates a flowchart illustrating an exemplary process 600 for updating a treatment plan based on a treatment record. In some embodiments, at least part of process 600 may be performed by the processing device 140 (implemented in, for example, the computing device 200 shown in FIG. 2). For example, the process 600 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 602, the acquisition module 410 may obtain an initial treatment plan related to a region of interest (ROI) of an object. The initial treatment plan may be a treatment plan determined before the course of a treatment. The initial treatment plan may include one or more initial treatment fractions. For example, the acquisition module 410 may obtain an initial treatment plan related to an ROI of a patient including N initial treatment fractions, where N is a natural number. An initial treatment fraction planned to be performed after a current initial treatment fraction (or referred to as a first initial treatment fraction) may be referred to as a subsequent initial treatment fraction or a second initial treatment fraction. For instance, between a first initial treatment fraction and a second initial treatment fraction, the second initial treatment fraction may be planned to be performed subsequent to the first initial treatment fraction. In some embodiments, many other treatment fractions may be performed before the first initial treatment fraction. An initial treatment plan may refer to the initial treatment plan before the treatment plan is updated with respect to an upcoming treatment fraction based on the actual performance of a current treatment fraction. Accordingly, an initial treatment plan may have been updated for one or more times with respect to treatment fractions that having been performed.

In some embodiments, based on a forecasting model and the initial treatment plan, the processing module 440 (e.g., the forecasting unit 540) may forecast that whether the ROI of the object transforms after the object is subjected to the treatment according to the initial treatment plan. In some embodiments, the acquisition module 110 may obtain the forecasting model related to a patient from the storage module 430 or from the storage device 140. The transformation of an ROI may include a shape change (e.g. volume change quantity) of the ROI and/or a position change of the ROI. The processing module 440 (e.g., the forecasting unit 540) may determine whether the initial treatment plan is suitable for a patient based on the forecasting model. For example, based on the forecasting model, if the shape change of the ROI or the position change quantity of the ROI does not satisfy the expectation of a doctor (for example, the position change exceeds an upper limit based on the forecastig model, or the shape change is under a lower limit based on the forecastig model) after the object receives the treatment according to the initial treatment plan or a portion thereof (e.g., a first initial treatment fraction of the initial treatment plan), the processing module 410 (e.g., the forecasting unit 540) nay deem the initial treatment plan unsuitable for the object. After the processing module 440 (e.g., the forecasting unit 540) deems the initial treatment plan unsuitable for the object, the acquisition module 410 may obtain another treatment plan from the storage module 430 or the storage device 140 to replace the initial treatment plan. Detailed description related to the forecasting model may be found elsewhere in the present disclosure. See, e.g., FIG. 7 and the description thereof.

In 604, an instruction may be sent to the imaging-treatment device 110 to deliver a treatment fraction, the first initial treatment fraction according to the initial treatment plan related to the ROI of the object. In some embodiments, the instruction may be generated by the processing module 440 and executed by the control module 420. The instruction may relate to an operation parameter set of the first initial treatment fraction. In some embodiments, the operation parameter set sent by the processing module 440 may be referred to as a planned operation parameter set. The imaging-treatment device 110 may deliver the first initial treatment fraction based on the operation parameter set of the first initial treatment fraction. In some embodiments, the operation parameter set actually performed by the imaging-treatment device 110 (e.g., the treatment component 116) may be referred to as an actual operation parameter set. In some embodiments, the instruction may be a real-time instruction according to which a treatment is delivered once or shortly after (e.g., within minutes, within hours, on the same day, etc.) the instruction is generated. The real-time instruction may cause the imaging-treatment device 110 to immediately or substantially immediately process the instruction and cause a treatment to be delivered to the object.

In some embodiments, the acquisition module 410 may obtain a first image of the ROI produced by a first scan of the ROI of the object. The first scan is performed before or during the first initial treatment fraction. In some embodiments, the acquisition module 410 may obtain the first image from a storage device in the radiation therapy system 100, such as the storage device 150.

In 606, the processing module 440 (e.g., treatment record generation unit 510) may generate a treatment record related to the first treatment fraction. The treatment record generation unit 510 may generate a treatment record related to the first initial treatment fraction. A treatment record may include the actual operation parameter set of the treatment component 116, describing how the treatment fraction of a treatment plan is actually performed by the radiotherapy device. In some embodiments, a deviation may exist between the treatment record of the first initial treatment fraction and the planned operation parameter set of the first initial treatment fraction. For example, the treatment component 116 may be unable to accurately perform the operation parameters of the first initial treatment fraction due to machine error. As another example, during the first treatment fraction, the object may be unable to bear the pain and abort the first treatment fraction, and some dose prescribed by the first initial treatment fraction is not delivered. Detailed description related to the generation of the treatment record may be found in FIG. 8 and the description thereof.

In 608, the processing module 440 (e.g., the treatment plan updating unit 530) may generate an updated second treatment fraction based on the second initial treatment fraction and the treatment record. The treatment plan updating unit 530 may update the initial treatment plan by updating the second initial treatment fraction of the initial treatment plan. The treatment plan updating unit 530 may determine whether a deviation exists between the actual operation parameter set of the treatment record and the planned operation parameter set of the first initial treatment fraction. If the treatment plan updating unit 530 determines that a deviation indeed exists between the actual operation parameter set of the treatment record and the planned operation parameter set of the first initial treatment fraction, the treatment plan updating unit 530 may update the planned operation parameter set of the second initial treatment fraction to generate an updated second treatment fraction based on the deviation. More descriptions of 608 may be found elsewhere in the present disclosures. See, e.g., FIG. 8 and the description thereof.

In some embodiments, the acquisition module 410 may obtain a second image of the ROT produced by a second scan of the ROT of the object. The second scan may be performed before or during the second treatment fraction (e.g., initial second treatment fraction or updated second treatment fraction, etc.) In some embodiments, the acquisition module 410 may obtain the second image from a storage device in the radiation therapy system 100, such as the storage device 150.

In some embodiments, the treatment plan updating unit 530 may generate an adaptive treatment plan based on the first image of the ROI and the second image of the ROT. After the object receives a treatment according to the first initial treatment fraction, the shape of the ROI or the position of the ROI may change. The treatment plan updating unit 530 may further update the second initial treatment fraction based on a difference between the shape of the ROI and/or the position of the ROI in the first image and the shape and/or the position of the ROI in the second image.

It should be noted that the above descriptions of the process 600 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 600 may include one or more other operations. However, those variations and modifications also fall within the scope of the present disclosure.

Figure 7:
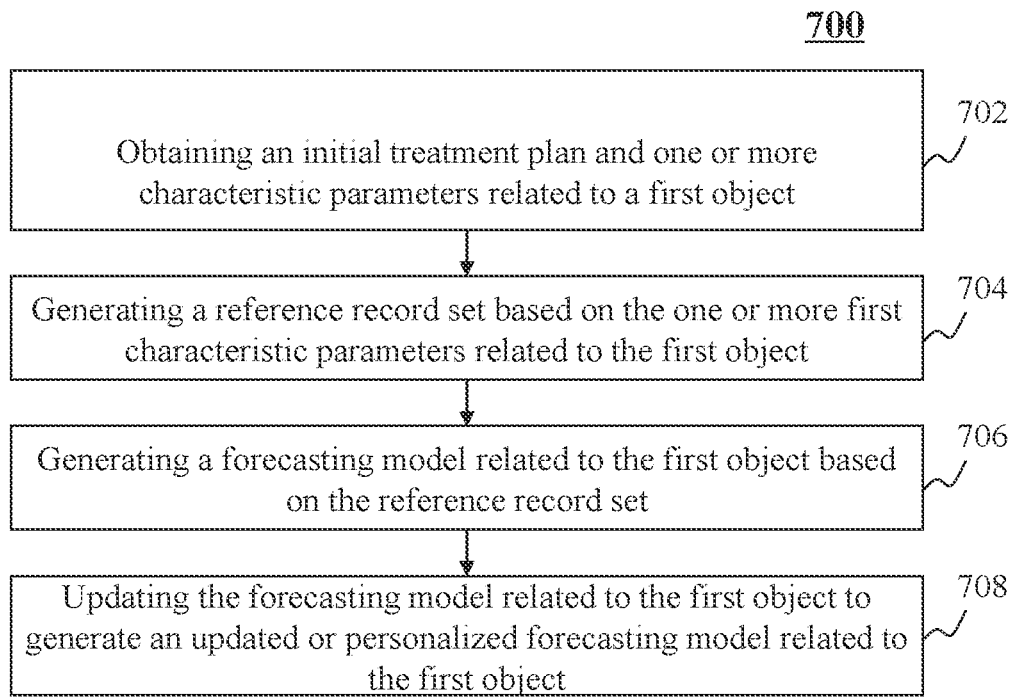
FIG. 7 illustrates a flowchart illustrating an exemplary process for forecasting therapeutic effects of a treatment plan performed on a patient according to some embodiments of the present disclosure.

FIG. 7 illustrates a flowchart illustrating an exemplary process for forecasting therapeutic effects of a treatment plan performed on an object. In some embodiments, at least part of process 700 may be performed by the processing device 140 (implemented in, for example, the computing device 200 shown in FIG. 2). For example, the process 700 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 702, the acquisition module 410 may obtain an initial treatment plan and one or more characteristic parameters related to a first object (e.g., a patient). A characteristic parameter may include at least one of an object characteristic parameter and a target characteristic parameter. The object characteristic parameter may represent a general characteristic of an object (e.g., the first object). For example, the object characteristic parameter related to the first object may include the age of the first object, or the gender of the first object, etc. The target characteristic parameter may represent a characteristic of a target, e.g., a tumor. If the target is a tumor, the target characteristic parameter may be referred to as a tumor characteristic parameter. For example, a tumor characteristic parameter related to the first object may include at least one of tumor location information of the first object, tumor type information of the object (e.g., lipoma, adenoma, fibroadenoma, adenocarcinoma, papillary cystadenocarcinoma, etc.), tumor size of the object (e.g., gross tumor volume), and tumor stage information of the object (cancer stage, e.g., stage 0, stage I, stage II, stage III, stage IV, etc.) In some embodiments, the characteristic parameter may further include a dose distribution related to the tumor. The dose distribution related to the tumor may be determined based on the tumor characteristic parameter and the initial treatment plan. In some embodiments, the acquisition module 410 may obtain the initial treatment plan of the first object and extract the characteristic parameter related to the first object from the initial treatment plan. In some embodiments, the acquisition module 410 may obtain a first treatment plan and a first parameter of a patient from the storage device 150 or user input via the communication port 240.

In 704, the forecasting unit 540 may retrieve a reference record set based on the one or more characteristic parameters related to the first object. The reference record set may represent a record set of one or more second objects similar with the first object in one or more characteristic parameters. For example, the reference set may include a reference record of a patient similar with the first object in terms of a tumor characteristic parameter. As another example, the reference record set may include a reference record of a second object who is subjected to a treatment plan similar to that of the first object.

The reference record set may include one or more reference records related to one or more second objects. A reference record related to a second object may provide at least one of a treatment plan related to the second object, one or more characteristic parameters related to the second object, and tumor progression history (recording, e.g., the shape, size, position of the tumor over a period of time) related to the second object. The tumor progression history may illuminate the tendency or trend how the tumor of a second object changes during a treatment plan. For example, a tumor progression history may be expressed as $\{(GTV_1, fraction_1), (GTV_2, fraction_2), \ldots (GTV_i, fraction_i), \ldots, (GTV_N, fraction_N)\}$. The number N may denote the total number of fraction in a treatment plan. $GTV_i$ may denote a gross tumor volume of a tumor before or after the delivery of the ith treatment fraction of the treatment plan.

The forecasting unit 540 may access a database (e.g., a database stored in the storage device 150) and retrieve one or more reference records related to the one or more second objects based on a similarity between the one or more characteristic parameters related to a first object and the one or more characteristic parameters related to one or more second objects. For example, the first object and the second object may have the same gender, or similar age, or similar treatment plan. A tumor size of the first object and a tumor size of the second object may be substantially similar with each other (e.g. within ±20% variation).

In 706, the forecasting unit 540 may generate a forecasting model related to the first object based on the reference record set. A forecasting model may forecast a tumor size (e.g., gross tumor volume) of an object before or after the delivery of a certain treatment fraction of a treatment plan. In some embodiments, the forecasting model may be generated based on a machine learning model. The machine learning model may include a convolutional neural network, an adaptive boosting model, a gradient boosting decision tree model, or the like, or any combination thereof. The forecasting unit 540 may train the machine learning model using the reference record sets as samples or training data to generate the forecasting model.

In 708, the forecasting unit 540 may update the forecasting model related to the first object to generate an updated or personalized forecasting model related to the first object. The forecasting unit 540 may obtain treatment images generated by scans before and/or after the first object receives one or more treatment fractions, and update the forecasting model based on the actual tumor characteristic parameter in the treatment images of the first object. For example, after the first object receives a treatment fraction, a $GTV_i$ (gross tumor volume) may be determined based on an image obtained by a scan performed after the treatment fraction, and the forecasting unit 540 may use the $GTV_i$ as a sample or training data to update the forecasting model.

It should be noted that the above descriptions of the process 700 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 700 may include one or more other operations. However, those variations and modifications also fall within the scope of the present disclosure.

Figure 8:
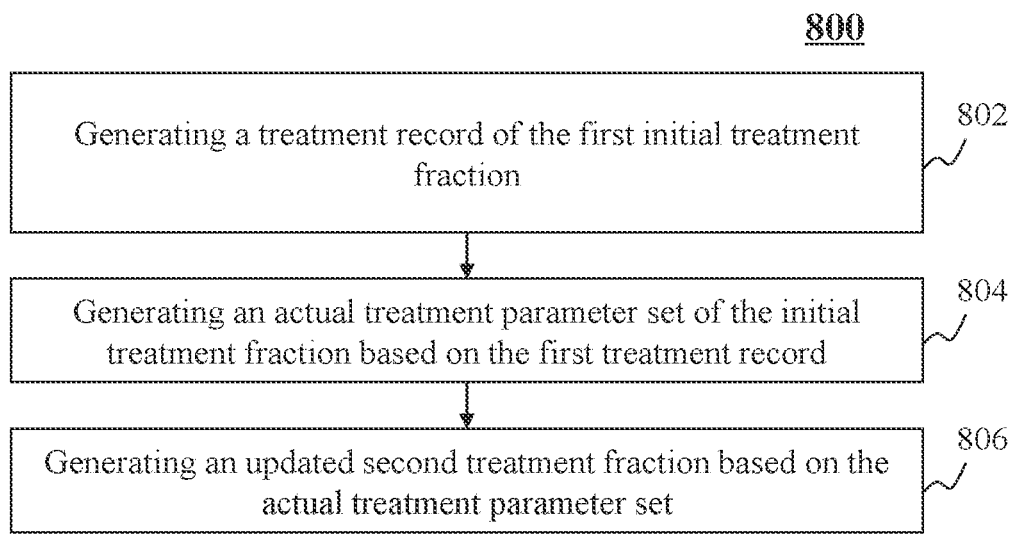
FIG. 8 illustrates a flowchart illustrating an exemplary process for updating an initial treatment plan according to some embodiments of the present disclosure.

FIG. 8 illustrates a flowchart illustrating an exemplary process for updating the initial treatment plan based on a treatment record. In some embodiments, at least part of process 800 may be performed by the processing device 140 (implemented in, for example, the computing device 200 shown in FIG. 2). For example, the process 800 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 802, the treatment record generation unit 510 may generate a treatment record of a first initial treatment fraction of an object. A treatment record may refer to an actual operation parameter set describing how a treatment fraction of a treatment plan is actually performed by a radiotherapy device (e.g., the treatment component 116). The treatment record may include one or more control records obtained during the performance of a treatment fraction (e.g., the first initial treatment fraction). The treatment record generation unit 510 may generate a control record at a regular time interval during the performance of a treatment fraction. For example, the treatment record generation unit 510 may generate a control record of the treatment record every 100 milliseconds during the performance of a treatment fraction that takes 5 minutes.

A control record may include one or more machine radiation parameters and/or one or more geometrical parameters related to the imaging-treatment device 110. The machine radiation parameter may include output data of an energy source (e.g., the radiation source 117). For instance, the machine radiation parameter may include a dose rate (e.g., MUs/min) of the radiation source 117, radiation duration of a radiation source 117 at a certain angle (e.g., 30 degrees), and a modality type provided by the radiation source 117 (e.g., photons, electrons, etc.) In some embodiments, the dose rate may be measured by an ionization chamber of the radiation source 117 (not shown in FIG. 1).

The geometrical parameter may include position information of a movement component (e.g., the table 114, the gantry 118, the collimator 119.) For instance, the geometrical parameter may include an angle of the gantry (e.g., the gantry 118), an angle of a collimator (e.g., the collimator 119), and a leaf setting parameter of a multi-leaf collimator (e.g., X1, X2, Y1, and Y2 values for individual leaves of the collimator 119, etc.), the position and/or angle of a table (e.g., the table 114).

In 804, the treatment parameter set generation unit 520 may generate an actual treatment parameter set of the initial treatment fraction based on the first treatment record. An actual treatment parameter set may be a treatment parameter set characterizing the one or more beam practically generated by the treatment component 116. The treatment record generation unit 510 may determine the actual treatment parameter set of the first initial treatment fraction based on the treatment record. For example, a field dose of the actual treatment parameter set may be determined based on the dose rate and the radiation duration at a specific angle. As another example, the radiation beam direction or the radiation beam shape of the actual treatment parameter set may be determined based on the geometrical parameter(s) of the treatment record.

In some embodiments, the treatment parameter set generation unit 520 may determine an actual dose distribution based on the actual treatment parameter set and the first image. The treatment parameter set generation unit 520 may apply the actual treatment parameter set to the first image to generate an actual delivered dose distribution of the treatment fraction. An actual delivered dose distribution may represent the radiation absorption rate related to one or more positions of the ROI during a treatment fraction. The dose distribution may be represented as $\{(A1, B1), (A2, B2), \ldots (Ai, Bi), \ldots (An, Bn)\}$, where Ai may denote a position of the ROI and Bi may denote the radiation dose absorbed by the position Ai of the ROI. For example, treatment parameter set generation unit 520 may extract a position Ai of the ROI from the first image, and look up the beam field applied to the position Ai based on the radiation beam direction and/or the radiation beam shape of the actual treatment parameter set, and determine the radiation dose absorbed by the position Ai based on the field dose of the actual treatment parameter set.

In some embodiments, the treatment parameter set generation unit 520 may output the actual treatment parameter set to a user via the I/O 230 or the I/O 350. In some embodiments, the treatment parameter set generation unit 520 may generate first visual information of a planned field related to the initial treatment plan. For instance, the first visual information may be an image including a plurality of pixels representing a planned field of the initial treatment plan. The treatment parameter set generation unit 520 may generate second visual information of an actual field related to the actual treatment parameter set. For instance, the second visual information may be an image including a plurality of pixels representing an actual field related to the actual treatment parameter set. The treatment parameter set generation unit 520 may output the first visual information and the second visual information to a user via the I/O 230 or the I/O 350.

A field may include one or more segments. The shape of the ROT may be regular (e.g., circular, square, triangle, etc.), or irregular. The field may include one or more segments with different shapes to conform to the shape of the ROI. In some embodiments, the treatment parameter set generation unit 520 may generate third visual information of a planned segment related to the initial treatment plan. For instance, the third visual information may be an image including a plurality of pixels representing a planned segment of the initial treatment plan. The treatment parameter set generation unit 520 may generate fourth visual information of an actual segment related to the actual treatment parameter set. For instance, the fourth visual information may be an image including a plurality of pixels representing an actual segment related to the actual treatment parameter set. The treatment parameter set generation unit 520 may output the third visual information and the fourth visual information to a user via the I/O 230 or the I/O 350.

In 806, the treatment plan updating unit 530 may generate an updated second treatment fraction based on the actual treatment parameter set. The treatment plan updating unit 530 may determine a deviation between the actual treatment parameter set of the first initial treatment fraction and the initial treatment parameter set of the first initial treatment fraction. TI update may relate to the dose difference and/or dose distribution difference between the first initial treatment fraction and the actually performed first initial treatment fraction. For example, if a dose received by the object during the first initial treatment fraction is lower than or exceeds the dose planned in the first initial treatment fraction, the treatment plan updating unit 530 may update the treatment plan by adjusting the second initial treatment fraction to make up for the deviation (e.g., the dose difference, the dose distribution difference), or by adjusting remaining initial treatment fractions (e.g., treatment fractions planned to be performed after the second initial treatment fraction) to make up for the deviation. In some embodiments, the treatment plan updating unit 530 may generate the updated second treatment fraction by changing the operation parameter set of the second initial treatment fraction.

It should be noted that the above descriptions of the process 800 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 800 may include one or more other operations. However, those variations and modifications also fall within the scope of the present disclosure.

Figure 9:
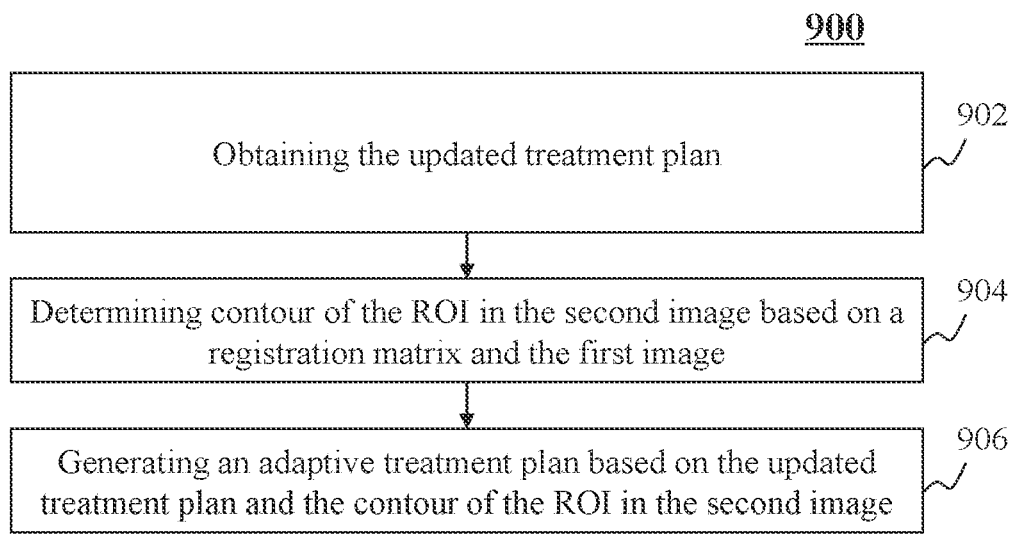
FIG. 9 illustrates a flowchart illustrating an exemplary process for generating an adaptive treatment plan according to some embodiments of the present disclosure.

FIG. 9 illustrates a flowchart illustrating an exemplary process for generate an adaptive treatment plan. In some embodiments, at least part of process 900 may be performed by the processing device 140 (implemented in, for example, the computing device 200 shown in FIG. 2). For example, the process 900 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In 902, the treatment plan updating unit 530 may obtain the updated second treatment fraction. Detailed description related to the generation of the updated second treatment fraction may be found elsewhere in the present disclosure. See, e.g., FIG. 8 and the description thereof.

In 904, the treatment plan updating unit 530 may determine the contour of the ROT in a second image based on a registration matrix and a first image. As the object may lose or gain weight during the treatment process, or the object may be positioned slightly different for different treatment fractions, the shape and/or position of the ROI before the first initial treatment plan may be different from shape and/or position of the ROI before the second initial treatment plan. In some embodiments, the contour of the ROI may be identified in the first image but not in the second image. In some embodiments, the contour of the ROI in the first image may be stored in the storage 150, e.g., according to user input.

The treatment plan updating unit 530 may register the second image with the first image, and generate a registration matrix between the first image and the second image. The first image may reflect the position and/or shape of the ROI before or during when the object receives the first treatment fraction. In some embodiments, the treatment plan updating unit 530 may obtain the first image of the ROI produced by a first scan of the ROI. In some embodiments, the acquisition module 410 may obtain the first image from a storage device in the radiation therapy system 100, such as the storage device 150. The first scan may be performed before or during a first treatment fraction. The second image may reflect the position and/or shape of the ROI before the patient receives an (updated) second treatment fraction following the first treatment fraction. In some embodiments, the acquisition module 410 may obtain the second image of the ROI produced by a second scan of the ROI. In some embodiments, the acquisition module 410 may obtain the second image from a storage device in the radiation therapy system 100, such as the storage device 150. The second scan may be performed before or during the second treatment fraction. A registration matrix may represent a transformation relationship between the ROI in the first image and the ROI in the second image. For example, if a pixel of the ROI has a coordinate A related to a coordinate system A in the first image and a pixel of the same ROI has a coordinate B related to a coordinate system B in the second image, the registration matrix may transform the coordinate A into the coordinate system B, or transform the coordinate B into the coordinate system A. The treatment plan updating unit 530 may generate the registration matrix based on, e.g., a linear transformation model or a non-rigid transformation model. The linear transformation model may include a rotation model, a scaling model, a translation model, an affine transformation model, or the like, or any combination thereof. The non-rigid transformation model may include a radial basis function, a physical continuum model (e.g., thin-plate or surface splines transformation, multiquadric transformation, and compactly-supported transformation, etc.), a large deformation model (e.g., diffeomorphisms, etc.), or the like, or any combination thereof. In some embodiments, the treatment plan updating unit 530 may determine a gross tumor volume of the second image based on the registration matrix and the gross tumor volume in the first image.

In 906, the treatment plan updating unit 530 may generate an adaptive treatment plan based on the updated second treatment fraction and the contour of the ROI in the second image. In some embodiments, the treatment plan updating unit 530 may obtain a function related to contour of the ROI and a treatment fraction. A treatment fraction may include one or more fields. A field may include one or more segments. In some embodiments, the shape of the ROI may be regular (e.g., circular, square, triangle, etc.), or irregular. The field may include one or more segments with different shapes to conform to the shape of the ROI. The treatment plan updating unit 530 may determine the shape of the ROI based on the contour of the ROT, and generate an adaptive treatment plan based on the function related to contour of the ROI and the treatment fraction and the updated second treatment fraction.

It should be noted that the above descriptions of the process 900 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 900 may include one or more other operations. However, those variations and modifications also fall within the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system, comprising:
    at least one storage medium including a set of instructions for adapting a treatment plan; and
    at least one processor configured to communicate with the at least one storage medium, wherein when executing the set of instructions, the at least one processor is configured to cause the system to:
        obtain an initial treatment plan of a region of interest, wherein the initial treatment plan includes a first initial treatment fraction and a second initial treatment fraction;
        obtain an actual treatment parameter set of the first initial treatment fraction; and
        generate an updated second treatment fraction based on the second initial treatment fraction and the actual treatment parameter set.

2. The system of claim 1, wherein to obtain the actual treatment parameter set of the first initial treatment fraction, the at least one processor is further configured to cause the system to:
    cause a radiation treatment device to deliver the first initial treatment fraction;
    obtain a treatment record related to the first initial treatment fraction; and
    generate the actual treatment parameter set of the first initial treatment fraction based on the treatment record.

3. The system of claim 2, wherein the actual treatment parameter set includes one or more machine radiation parameters related to the radiation treatment device and one or more geometrical parameters related to the radiation treatment device.

4. The system of claim 3, wherein the one or more machine radiation parameters related to the radiation treatment device include a dose rate, a delivery duration of a beam, or a modality type of the beam.

5. The system of claim 4, wherein the one or more geometrical parameters relating to the radiation treatment device include at least one of position information of a table of the radiation treatment device, position information of a gantry of the radiation treatment device, or position information of a collimator of the radiation treatment device.

6. The system of claim 1, wherein the at least one processor is further configured to cause the system to:
    determine one or more transformations of the region of interest based on a forecasting model and the initial treatment plan.

7. The system of claim 6, wherein to generate the forecasting model, the at least one processor is further configured to cause the system to:
    obtain one or more characteristic parameters related to a first object;
    retrieve a reference record set based on the one or more first characteristic parameters related to the first object;
    generate a forecasting model related to the first object based on the reference record set; and
    update the forecasting model based on the initial treatment plan.

8. The system of claim 7, wherein the reference record set includes a reference record of a second object.

9. The system of claim 8, wherein the at least one processor is further configured to cause the system to:
    retrieve the reference record set based on a similarity between the one or more characteristic parameters related to the first object and one or more characteristic parameters related to the second object.

10. The system of claim 7, wherein the one or more characteristic parameters include at least one of an age of the first object, a gender of the first object, tumor location information of the first object, a tumor type of the first object, a tumor size of the first object, tumor stage information of the first object, or a dose distribution related to a tumor.

11. The system of claim 1, wherein the first initial treatment fraction includes an initial treatment parameter set, and to generate the updated second treatment fraction based on the second initial treatment fraction and the actual treatment parameter set, the at least one processor is further configured to cause the system to:
    determine a deviation between the actual treatment parameter set of the first initial treatment fraction and the initial treatment parameter set of the first initial treatment fraction; and
    generate the updated second treatment fraction based on the second initial treatment fraction and the deviation.

12. The system of claim 1, wherein to generate the updated second treatment fraction, the at least one processor is further configured to cause the system to:
    obtain a first image of the region of interest by a first scan of the region of interest and a second image of the region of interest by a second scan of the region of interest;
    determine a contour of the region of interest in the second image based on a registration matrix and the first image; and
    determine the updated second treatment fraction based on the contour of the region of interest.

13. The system of claim 12, wherein the registration matrix is a non-rigid registration matrix.

14. The system of claim 1, wherein the at least one processor is further configured to cause the system to:
    output the actual treatment parameter set to a user.

15. The system of claim 1, wherein the at least one processor is further configured to cause the system to:
    generate first visual information of a planned beam related to the treatment plan;
    generate second visual information of an actual beam related to the actual treatment parameter set; and
    output the first visual information and the second visual information to the user.

16. The system of claim 1, wherein the at least one processor is further configured to cause the system to:
    generate third visual information of a planned segment related to the treatment plan;
    generate fourth visual information of an actual segment related to the actual treatment parameter set; and
    output the third visual information and the fourth visual information to the user.

17. A method implemented on a computing device having at least one processor and at least one computer-readable storage medium, the method comprising:

obtaining an initial treatment plan of a region of interest, wherein the initial treatment plan includes a first initial treatment fraction and a second initial treatment fraction;

obtaining an actual treatment parameter set of the first initial treatment fraction; and generating an updated second treatment fraction based on the second initial treatment fraction and the actual treatment parameter set.

18. The method of claim 17, wherein the obtaining an actual treatment parameter set of the first initial treatment fraction includes:

causing a radiation treatment device to deliver the first initial treatment fraction;

obtaining a treatment record related to the first initial treatment fraction; and generating the actual treatment parameter set of the first initial treatment fraction based on the treatment record.

19. The method of claim 17, further comprising:

determining one or more transformations of the region of interest based on a forecasting model and the initial treatment plan.

20. A non-transitory computer readable medium, comprising at least one set of instructions for image storage, wherein when executed by one or more processors of a computing device, the at least one set of instructions causes the computing device to perform a method, the method comprising:

obtaining an initial treatment plan of a region of interest, wherein the initial treatment plan includes a first initial treatment fraction and a second initial treatment fraction;

obtaining an actual treatment parameter set of the first initial treatment fraction; and generating an updated second treatment fraction based on the second initial treatment fraction and the actual treatment parameter set.

* * * * *